United States Patent
Hollmann et al.

(10) Patent No.: US 8,313,935 B2
(45) Date of Patent: Nov. 20, 2012

(54) METHOD FOR ISOLATING POLYHYDROXYL ALKANOATES

(75) Inventors: Rajan Hollmann, Worms (DE); Bryan Cooper, Mannheim (DE); Peter Preishuber-Pfluegl, Ludwigshafen (DE); Arnold Schneller, Seeheim-Jugenheim (DE)

(73) Assignee: BASF SE, Ludwigshafen (DE)

( * ) Notice: Subject to any disclaimer, the term of this patent is extended or adjusted under 35 U.S.C. 154(b) by 191 days.

(21) Appl. No.: 13/002,404

(22) PCT Filed: Jun. 30, 2009

(86) PCT No.: PCT/EP2009/058153
§ 371 (c)(1),
(2), (4) Date: Jan. 3, 2011

(87) PCT Pub. No.: WO2010/000719
PCT Pub. Date: Jan. 7, 2010

(65) Prior Publication Data
US 2011/0112274 A1    May 12, 2011

(30) Foreign Application Priority Data
Jul. 2, 2008 (EP) .................. 08159484

(51) Int. Cl.
*C12P 7/62* (2006.01)
*C08G 63/06* (2006.01)
(52) U.S. Cl. ....................... 435/135; 528/361
(58) Field of Classification Search .......... 435/135; 528/361
See application file for complete search history.

(56) References Cited

U.S. PATENT DOCUMENTS 7,393,668 B2 * 7/2008 Yanagita et al. ............. 435/135
2010/0233768 A1   9/2010 Cooper et al.

FOREIGN PATENT DOCUMENTS

| DE | 19712702 A1 | 10/1998 |
| WO | WO-2005/052175 A2 | 6/2005 |
| WO | WO-2007/082836 A1 | 7/2007 |
| WO | WO-2007/135039 A1 | 11/2007 |

OTHER PUBLICATIONS

Barnard et al., "The Poly-β-hydroxybutyrate Granule in Vivo: A New Insight Based on NMR Spectroscopy of Whole Cells", *The Journal of Biological Chemistry*, vol. 264, No. 6, pp. 3286-3291 (1989).
Jung et al., "Spontaneous liberation of intracellular polyhydroxybutyrate granules in *Escherichia coli*", *Research in Microbiology*, vol. 156, pp. 865-873 (2005).
Ling et al., "Recovery of poly-3-hydroxybutyrate from recombiant *Escherichi coli* by homogenization and centrifugation", *Biotechnology Techniques*, vol. 11, No. 6, pp. 409-411 (1997).
Kopinke et al., "Thermal Decomposition of biodegradable polyesters—I: Poly(β-hydroxybutyric acid)", *Polymer Degradation and Stability*, vol. 52, pp. 25-38 (1996).

* cited by examiner

*Primary Examiner* — Herbert J Lilling
(74) *Attorney, Agent, or Firm* — Connolly Bove Lodge & Hutz LLP

(57) ABSTRACT

The invention relates to a method for isolating polyhydroxyalkanoates from production cells which comprises
i) disintegrating the production cells, subsequently
ii) separating off the cell fragments from the polyhydroxyalkanoate grains by means of a continuous jet separator;
iii) the concentrated polyhydroxyalkanoate grains are washed with an aqueous alkali solution and then
iv) with an aqueous acid.

10 Claims, No Drawings

METHOD FOR ISOLATING POLYHYDROXYL ALKANOATES

PRIORITY

Priority is claimed as a national stage application, under 35 U.S.C. §371, to PCT/EP2009/058153, filed Jun. 30, 2009, which claims priority to European application 08159484.8, filed Jul. 2, 2008. The disclosures of the aforementioned priority applications are incorporated herein by reference in their entirety.

The invention relates to a method for isolating polyhydroxyalkanoates from a production cell.
i) disintegrating the production cells, subsequently
ii) separating off the cell fragments from the polyhydroxyalkanoate grains by means of a continuous jet separator;
iii) the concentrated polyhydroxyalkanoate grains are washed with an aqueous alkali solution and then
iv) with an aqueous acid.

Polyhydroxyalkanoates (PHAs), such as polyhydroxybutyrates (PHBs) for example, can be synthesized using bacteria. For example, such biotechnological methods are described in Biopolymer, Wiley-VCH, 2002.

PHB occurs at the end of fermentation in the bacterial cells in the form of grains which are surrounded by a protein envelope (J. Biol. Chem. 1989, vol. 264(6), pages 3286-3291). To obtain a sufficiently pure PHB, it must be separated from the bacterial cells.

The biotechnologically produced crude mixtures, in addition to the desired polyhydroxyalkanoate, comprise the microorganisms which have produced the polyhydroxyalkanoate (production cells, biomass, or non-polyhydroxyalkanoate mass). The polyhydroxyalkanoate can be isolated from the biomass a) by dissolving the biomass, b) by extraction of the polyhydroxyalkanoate in a suitable extraction medium or c) by mechanical disintegration of the biomass (production cell) and subsequent separation of the cell fragments from the polyhydroxyalkanoate (PHA)-grains.

The most frequent method for this is extraction of the PHA grains from the biomass using a solvent (workup b)). The use of solvents has a number of disadvantages as a consequence. One is forced to invest in complex and costly infrastructure for handling and recovering the solvents. The extracted biomass must be freed from the solvent residues before further use as fertilizer or feedstuff. Since PHB dissolves only unsatisfactorily in many solvents, the amounts of solvent which are required are very high.

For breakdown and dissolution of the biomass (workup a)), use can be made of, for example, enzymes or chemical methods. In addition, surface-active compounds can be added. A combination of a plurality of methods is possible. The release of the polyhydroxybutyrate (PHB) formed from genetically modified *Escherichia coli* cells has been described in Research In Microbiology 2005, 156, pages 865-873. Here an autolysis step is provided afterwards. The exact autolysis conditions are not described. Autolysis is a process of self-dissolution of the cells by their own enzymes. This preparation method has the following disadvantages. Since the autolysis proceeds incompletely and cell fragments and also PHB grains still adhere to one another, only approximately 80% of the PHB formed is released.

An interesting mechanical workup c) is described in WO 2007/135039. The production cells are disrupted by means of a high-pressure homogenizer device and the cell fragments of the production cells are separated off from the polyhydroxyalkanoate grains formed via a jet separator. This method is highly efficient when production cells having a very high polyhydroxyalkanoate fraction are used as starting material. In other cases, separating off the cell fragments (cell walls) does not always succeed completely satisfactorily. Proteinaceous (nitrogenous) impurities lead to color changes (see Biotechnology Techniques, Vol. 11, No. 6, June 1997, page 411, left-hand column, last paragraph) and to a lower thermal stability of the polyhydroxyalkanoates (Polymer Degradation and Stability 52 (1996), page 38, left-hand column).

The object is therefore to find a method which leads to complete separation of cell fragments of the production cell from the polyhydroxyalkanoate grains formed.

This object is outstandingly achieved by the four-stage workup mentioned at the outset. The method is consequently distinguished from the conventional methods by high efficiency, economic viability and excellent processing ability.

The necessary equipment is technically available and upscalable as desired, and so the method can be applied without problems to the industrial scale.

A particular embodiment of the inventive method disintegrates the production cells mechanically in step i). The chemical-free disintegration has advantages. It has been described that cells of the PHB-producing bacterium *Alcaligenes eutrophus* can be disintegrated using a homogenizer (Bioseparation 1991, 2, pages 155-166). The PHB grains present in the cells were virtually completely extracted from the cells after four passages through a homogenizer. The cell suspension, in this type of homogenizer, is pressed through a valve. By adjusting the gap width between valve cone and valve seat, turbulence is generated. The suspension exiting from the valve then impacts a steel plate. The pressure of this machine is therefore restricted to 1500 bar.

To generate higher pressures, large amounts of electrical power are required. Cell disintegration using a homogenizer is economic in particular when the cells are completely disintegrated after a single passage. The method described in Bioseparation 1991, 2, pages 155-166, has the disadvantage that four passages through the homogenizer are required.

We have now established that PHA-comprising cells of, in particular, *Alcaligenes eutrophus* may be very readily disintegrated using a high-pressure homogenizer as described hereinafter. In this case, in a single passage through the high-pressure homogenizer at a pressure of 2000 and more bar, over 99% of the cells are disintegrated and PHA virtually completely released. The present invention therefore also relates to disintegration by means of a high-pressure homogenizer which operates at pressures of 2000 and more atm. For example, it comprises the following arrangement:

Examples of suitable homogenizing devices:
a) comprises an orifice plate having at least one inlet nozzle and an orifice plate having at least one outlet nozzle, in the intermediate space between the orifice plates, if appropriate, mechanical energy being introduced or
b) comprises an orifice plate having at least one inlet nozzle and an impact plate, in the intermediate space between the orifice plate and the impact plate, if appropriate, mechanical energy being introduced.

EMBODIMENT A)

The homogenizing device for isolating the polyhydroxyalkanoates comprises, for example, an orifice plate having at least one inlet nozzle and an orifice plate having at least one outlet nozzle, the nozzles being arranged axially to one another. In the intermediate space between the orifice plates a static mixer can be situated. If appropriate, in the intermediate space, mechanical energy is additionally introduced.

The orifice plates which can be used according to the inventive method have at least one orifice, that is at least one nozzle. The two orifice plates can each have any desired number of orifices, but preferably no more than in each case 5 orifices, particularly preferably no more than in each case three orifices, very particularly preferably no more than in each case two orifices, and in particular preferably no more than in each case one orifice. Both orifice plates can have a different number or the same number of orifices, preferably both orifice plates have the same number of orifices. Generally, the orifice plates are perforated plates each having at least one orifice.

In another embodiment of this inventive method, the second orifice plate is replaced by a sieve, that is the second orifice plate has a multiplicity of orifices or nozzles. The sieves which can be used can cover a large range of pore sizes, generally the pore sizes are between 0.1 and 250 μm, preferably between 0.2 and 200 μm, particularly preferably between 0.3 and 150 μm, and in particular between 0.5 and 100 μm.

The orifices or nozzles can have any conceivable geometric shape, they can, for example, be circular, oval, polygonal having any desired number of edges, which if appropriate can also be rounded, or else star-shaped. Preferably, the orifices have a circular shape.

The orifices of the inlet orifice plate generally have a diameter of from 0.05 mm to 1 cm, preferably from 0.08 mm to 0.8 mm, particularly preferably from 0.1 to 0.5 mm, and in particular from 0.2 to 0.4 mm. The orifices of the outlet orifice plate generally have a diameter of from 0.5 mm to 1 cm, preferably from 5 mm to 50 mm, particularly preferably from 10 to 20 mm.

The two orifice plates are preferably constructed in such a manner that the orifices or nozzles are arranged axially to one another. Axial arrangement is to be taken to mean that the flow direction generated by the geometry of the nozzle orifice is identical for the two orifice plates. The orifice directions of the inlet nozzle and outlet nozzle for this need not lie on a line, they can also be displaced in parallel, as follows from the above statements. Preferably, the orifice plates are directed in parallel.

However, other geometries are possible, in particular non-parallel orifice plates, or different orifice directions of the inlet and outlet nozzles. In the two-orifice-plate system (inlet orifice plate and outlet orifice plate), as set forth above, the outlet nozzle has larger orifices. As a result, the turbulence is calmed. An impact plate is not necessary in this case.

The thickness of the orifice plates can be as desired. Preferably, the orifice plates have a thickness in the range of from 0.1 to 100 mm, preferably from 0.5 to 30 mm, and particularly preferably from 1 to 10 mm. The thickness (I) of the orifice plates is selected in such a manner that the quotient of diameter (d) of the orifices and thickness (I) is in the range of 1:1, preferably 1:1.5, and particularly preferably 1:2.

The intermediate space between the two orifice plates can be as long as desired, generally the length of the intermediate space is 1 to 500 mm, preferably 10 to 300 mm, and particularly preferably 20 to 100 mm.

In the intermediate space between the orifice plates, a static mixer can be situated which can completely or partially fill up the section between the two orifice plates. Preferably, the static mixer extends over the entire length of the intermediate space between the two orifice plates. Static mixers are known to those skilled in the art. A static mixer can be, for example, a valve mixer, or a static mixer having boreholes, one made of fluted lamellae, or one made of engaging ribs. In addition, it can be a static mixer in spiral shape or in an N shape, or one having heatable or coolable mixing elements.

In addition to the static mixer, in the intermediate space between the two orifice plates, mechanical energy can be introduced. The energy can be introduced, for example in the form of mechanical vibrations, ultrasound or rotational energy. As a result, a turbulent flow is produced which has the effect that the particles do not agglomerate in the intermediate space.

EMBODIMENT B)

Alternatively to this first variant, the mixing device can comprise an orifice plate having at least one inlet nozzle and an impact plate, in the intermediate space between the orifice plate and the impact plate, if appropriate, a static mixer being situated. Alternatively, or in addition to the static mixer, mechanical energy can be introduced in the intermediate space.

The aforesaid applies to the orifice plate having inlet nozzle, the intermediate space having a static mixer and mechanical energy introduction.

In this variant, the second orifice plate is replaced by an impact plate. The impact plate generally has a diameter which is 0.5 to 20%, preferably 1 to 10%, smaller than the tubular diameter at the point at which the impact plate is installed.

In general, the impact plate can have any geometrical shape, preferably in the form of a round disk, so that, in frontal view, a ring gap may be seen. The form of a slot or a channel, for example, is also conceivable.

The impact plate, in a similar manner to the second orifice plate in the abovedescribed variant, can be affixed at different distances with respect to the first orifice plate. As a result, the intermediate space between the orifice plate and the impact plate can be of any desired length; generally, the length of the intermediate space is 1 to 500 mm, preferably 10 to 300 mm, and particularly preferably 20 to 100 mm.

The inventive method has some advantages over the methods known from the prior art, since particularly high yields of the polyhydroxyalkanoate of high molecular weight are obtained. In particular, polyhydroxyalkanoates having Mn of 50 000 to 2 000 000, and in particular from 100 000 to 200 000, may be achieved by this workup variant.

The temperature at which the crude emulsion is emulsified to give the finely divided emulsion by the inventive method is generally 0 to 150° C., preferably 5 to 80° C., particularly preferably 20 to 40° C. In this case all of the homogenizing units used in the device can be heated/cooled.

The homogenization is generally carried out at pressures above atmospheric pressure, that is >1 bar. In this case, however, the pressures do not exceed a value of 10 000 bar, so that preferably homogenization pressures of >1 bar to 10 000 bar, preferably 5 to 2500 bar, and particularly preferably from 100 to 2000 bar, are established.

The production cell concentrations used in the inventive method are about 20 to 300 g/l, preferably 50-220 g/l.

Any type of cell or cell layer in this case is termed production cell; in particular those cells of animal, plant or microbial origin. Equally preferably, production cells are recombinant organisms. Particularly highly suitable production cells are prokaryotes (including the Archaea) or eukaryotes, particularly bacteria, including halobacteria and methanococci, fungi, insect cells, plant cells and mammal cells, particularly preferably *Alcaligenes eutrophus, Escherichia coli, Bacillus subtilis, Bacillus megaterium, Aspergillus oryzea, Aspergillus nidulans, Aspergillus niger, Pichia pastoris, Pseudomonas* spec., *Lactobacillen, Hansenula polymorpha, Tricho-*

*derma reesei*, SF9 (or related cells). Particularly preferably, the microorganism is *Alcaligenes eutrophus*.

The production cell can be used in the inventive method directly after culturing (e.g. fermentation); but it is also possible first to kill the production cell, for example by sterilization, and if appropriate to enrich the cell mass by filtration of the culture medium.

Polyhydroxyalkanoates are taken to mean biotechnologically produced polymers. In particular, these are taken to mean the following: poly(3-hydroxybutyrate) (P-3HB), poly (3-hydroxybutyrate)/co-3-hydroxyvalerate (P-3HBco-3HV), poly(3-hydroxybutyrate)/co-4-hydroxybutyrate (P-3HB-co-4HB), poly(3-hydroxybutyrate)/co-3-hydroxyhexanoate (P-3HB-co-3HHx) and poly(3-hydroxybutyrate)/co-3-hydroxyoctanoate (P-3HB-co-3HO).

In step ii), the cell fragments are separated from the polyhydroxyalkanoate grains by means of a continuous jet separator. The pellet comprising the polyhydroxyalkanoate grains is continuously removed by the jets, while the cell fragments are effectively separated off continuously in the overflow (actually "clear flow"). There is no emptying due to opening the drum and thereby also no losses, vortexes and similar instabilities, which are at the expense of an efficient separation. In order to achieve a still higher purity, the PHA grains can be admixed with clear water and again centrifuged. In this manner an aqueous suspension of PHA grains of impressive purity is achieved, which can then be dried in a known manner, for example by spray drying. Using the following steps iii) and iv), this can be dramatically lowered.

Jet separators are also known under the term Westfalia Separator. A detailed description may be obtained under www.gea-westfalia.de, for example. By way of example the VisCon® system may be cited, in which the jets are viscosity controlled. This avoids the adaptation of the separator parameters (emptying times) under changed feed conditions and as a consequence thereof, constant solid discharge concentrations are achieved. In the VisCon® system, the jets are not situated on the drum rim, but on a smaller diameter in the drum. Introduction via the hydrohermetic feed and also the outlet via the jets increases the cell activity of the separated cells.

In step iii), the previously concentrated polyhydroxyalkanoate grains are washed with an aqueous alkali solution.

Alkali solution is taken to mean generally hydroxides such as alkaline earth metal hydroxides, and in particular alkali metal hydroxides, carbonates such as alkaline earth metal carbonates and in particular alkali metal carbonates, and hydrogencarbonates such as alkaline earth metal hydrogencarbonates and, in particular, alkali metal hydrogencarbonates.

Hydroxides are preferably used in a concentration of 0.01 to 1 mol/l. Carbonates and hydrogencarbonates are generally used in a concentration of 0.01 to 2 mol/l.

The treatment with alkali solution can be carried out at temperatures between 0 and 120° C., preferably 10 to 60° C. As already mentioned above, the temperature in the method according to the invention is selected in such a manner that no significant amounts of polyhydroxyalkanoate (<5%) pass into solution.

Using the alkali solution, generally a hydroxide final concentration of 0.001 to 1 mol/l is set, preferably 0.01 to 0.5 mol/l, and in particular 0.05 to 0.2 mol/l.

After the treatment with alkali solution, the polymer is removed from the aqueous solution. This can be performed, for example, by filtration, centrifugation, sedimentation or by means of a hydrocyclone.

The alkali solution used can be in solid or liquid form for this purpose.

By means of a treatment with an acid in step iv), the content of alkali metals and alkaline earth metals of the polyhydroxyalkanoate grains can be reduced and the thermal stability of the polyhydroxyalkanoates thereby increased.

The treatment with acid can be understood as a washing process. In contrast to the method described in DE 19712702, in the method according to the invention, the polyhydroxyalkanoates are not dissolved by the acid.

The acids according to the invention comprise not only Lewis acids but also Bronsted acids. Lewis defines an acid as a substance which has an electrophilic electron pair acceptor. According to the definition by Bronsted, an acid is a compound that can release protons to reaction partners.

The acid can be present as solid, liquid or gas. In addition, the acid can be present as a solution in an organic solvent or water.

Particularly preferred are aqueous acids. Mineral acids are preferably used in a concentration of 0.01 to 1 mol/l. Carboxylic acids and sulfonic acids are generally used in a concentration of 0.01 to 2 mol/l.

As liquid acids, inorganic or organic acids are used. Preferred acids are sulfuric acid, hydrochloric acid, phosphoric acid, phosphonous acid, nitric acid, nitrous acid, carbonic acid, silicic acid, hypochlorous acid, perchloric acid, amidosulfonic acid, acetic acid, formic acid, propionic acid, sulfonic acid, sulfonous acid, methanesulfonic acid, trifluoromethanesulfonic acid or citric acid.

Preferred gaseous acids are $SO_2$, $SO_3$ or $CO_2$.

The polyhydroxyalkanoate can be present during the treatment in solution, as a slurry, as a melt or as a solid.

The treatment with acid can be carried out continuously or discontinuously.

The treatment with acid can be carried out at temperatures between 0 and 120° C., preferably 10 to 60° C. As already mentioned above, the temperature in the method according to the invention is selected in such a manner that no significant amounts of polyhydroxyalkanoate (<5%) pass into solution.

Using the acid, generally an acid end concentration of 0.001 to 1 mol/l, preferably 0.01 to 0.5 mol/l, and in particular 0.05 to 0.2 mol/l is set.

After the treatment with acid, the polymer is removed from the aqueous solution. This can be performed, for example, by filtration, centrifugation, sedimentation or by means of a hydrocyclone.

The acid used can be present in liquid, solid or gaseous state for this purpose.

A preferred form is the use of a solid acid. Solid acid is taken to mean, in particular, ion exchangers. An alternative is the use of ion exchangers having acid groups such as sulfonic acids, phosphoric acids and carboxylic acids.

The acid can be present as a gas. The excess acid can be removed by degassing the polyhydroxyalkanoate solution or by extracting the gaseous acid into a second liquid phase.

For further reduction of the nitrogen content, a bleaching step (step v)) can be introduced. Suitable bleaching agents are 0.001 to 0.2 M hypochlorite and/or hydrogen peroxide solution. If alkali metal hypochlorite is used, it can be advantageous to carry out the bleaching step v) directly subsequently to step iii) and finally to wash with acid (step iv)). In some cases it has proved to be advantageous to carry out the bleaching step vi-1) subsequently to the acid washing operation (iv).

Equipment Used:

In the example, as high-pressure homogenizer for disintegrating the production cells, the following arrangement I was selected. As inlet nozzle, use was made of an orifice plate having 14×0.2 mm wide boreholes. The fermentation broth was a suspension and was forced through the orifice plate at a pressure of approximately 2000 atm. In the intermediate space (15 mm long and 8 mm in diameter), the suspension was vortexed before it encountered the second orifice plate which acted as outlet nozzle. The cell suspension was passed through a conical borehole to the outlet orifice plate and then exited from the orifice plate block from a single borehole (diameter 1.5 mm). The outlet orifice plate was centrally arranged compared with the boreholes of the inlet nozzle.

As jet separator, use was made of an instrument from the company GEA Wesffalia type HFC-15.

EXAMPLE 1A

Isolation of 3-hydroxypolyhydroxybutyrate (3-PHB) from *E. coli* Production Cells i) The method started from 200 l of an *E. coli* fermentation broth having a content of 57.7 g/l of bio dry mass, thereof of 60.6% 3-polyhydroxybutyrate, cooled to 4° C. in the fermenter. The fermentation proceeded according to B. S. Kim, S. Y. Lee, H. N. Chang in Biotechnology Letters, Vol. 14, pages 811-816 (1992). The culture broth was passed in entirety through a high-pressure homogenizer at 1750 bar pressure and cooled to 12° C. at the outlet. The cell homogenate was then diluted with deionized water to a solids content of 22.3 g/l.
ii) In a type HFC-15 jet separator from GEA Westfalia, at a feed rate of 700 l/h, PHB particles (concentrate) and cell debris (overflow) were separated. The total dry matter in the concentrate was 110.1 g/l, thereof of 90% 3-PHB. In the overflow there were 7.7 g/l of total dry matter, thereof of 8.6% 3-PHB.
iii) The concentrate was admixed with KOH to an end concentration of 0.2 mol/l and stirred for 1 h at 30° C. Thereafter the mixture was centrifuged, the supernatant was discarded and the pellet resuspended in deionized water, centrifuged again and the supernatant again discarded (washing step).
iv) A washing step followed using sulfuric acid in an end concentration of 0.1 mol/l, and also a further washing step with deionized water. The drying proceeded in a vacuum drying cabinet at 40° C.

COMPARATIVE EXAMPLE 1B

The procedure of steps i), ii) and iv) was performed in a similar manner to Example 1a. The intermediate step iii) (washing with KOH) was dispensed with.

For Example 1a and Comparative Example 1b, 3-PHB content, total nitrogen, potassium content and also molecular weight of the samples before ($M_w1$) and after ($M_w2$) a thermal stress of 185° C. over a period of 35 minutes were determined. The results are listed in the table hereinafter.

| No. | PHB content (%) | Nitrogen (%) | Potassium (ppm) | $M_n1$ | $M_w1$ | $M_n2$ | $M_w2$ |
|---|---|---|---|---|---|---|---|
| 1a | 99.9 | 0.17 | 50 | 258,000 | 1,540,000 | 58,000 | 153,000 |
| C1b | 95.5 | 1.1 | 70 | 245,000 | 1,420,000 | 12,700 | 32,900 |

The polymer from Example 1 is, owing to the lower contamination with proteins and DNA (lower nitrogen content), significantly more stable under thermal stress. During thermal stress, as occurs typically during a processing, in Example 1a, a smaller breakdown of the molecular weight occurs. The thermal stability was determined via the decrease in melt viscosity at a temperature between 175 and 185° C. (see P. A. Daly et al., J. of Applied Polymer Science, Vol. 98, pages 66 to 74 (2005); in particular FIG. 4 and equation 5). The thermal stability of the polymers investigated may be related on the basis of the gradient of the lines. The lower the gradient of the lines, the more thermally stable is the material in question. Example 1 had a significantly lower gradient than a 3-PHB produced by solvent extraction—as described in WO2005052175.

For further reduction of the nitrogen content, a bleaching step can follow. The bleaching of a 5% (w/w) suspension of the product for variant 1 in 0.08 mol/l of sodium hypochlorite for 15 minutes at room temperature with subsequent washing steps with deionized water reduced the nitrogen content to 0.018%.

EXAMPLE 2A

Isolation of 3-hydroxy-polyhydroxybutyrate (3-PHB) from *E. coli* Production Cells i) The method started from 200 l of an *E. coli* fermentation broth having a content of 66.7 g/l of bio dry mass, thereof of 61.5% PHB, cooled to 4° C. in the fermenter. The fermentation proceeded according to B. S. Kim, S. Y. Lee and H. N. Chang in Biotechnology Letters, Vol. 14, pages 811-816 (1992). The culture broth was passed in entirety through a high-pressure homogenizer at 1750 bar pressure and not cooled at the outlet. The cell homogenate was then diluted with deionized water to a solids content of 16.3 g/l.
ii) In an HFC-15 type jet separator from GEA Westfalia, PHB particles (concentrate) and cell debris (overflow) were separated at a feed rate of 700 l/h. The total dry matter in the concentrate was 50.6 g/l, thereof of 90% PHB. In the overflow there was 0.7 g/l of total dry matter, thereof of 25.6% PHB.
iii) The concentrate was admixed with NaOH at an end concentration of 0.2 mol/l and stirred for 1 h at 30° C. Thereafter the mixture was centrifuged, the super-natant was discarded and the pellet resuspended in deionized water, centrifuged again and the supernatant again discarded (washing step).
iv) A washing step with sulfuric acid at an end concentration of 0.1 mol/l followed, and also a further washing step with deionized water. The drying proceeded in a vacuum drying cabinet at 40° C.

Example 2b) was carried out in a similar manner to Example 2a, only, in step iii), KOH was used instead of NaOH.

Example 2c) was carried out in a similar manner to Example 2a, only, in step iii), NaOH was added up to an end concentration of 0.1 mol/l and stirring was carried out for 0.5 h at 30° C.

Comparative Example 2d was carried out as for Example 2a, but step iii) was dispensed with.

For Examples 2a to 2c and Comparative Example 2d, 3-PHB content, total nitrogen, potassium content and also molecular weight of the samples were determined. The results are summarized hereinafter in a table.

| No. | PHB content (%) | Nitrogen (%) | Potassium or sodium (ppm) | $M_n$ | $M_w$ |
|---|---|---|---|---|---|
| 2a | 98 | 0.23 | <30 | 344,000 | 1,020,000 |
| 2b | 99 | 0.24 | <30 | 374,000 | 1,290,000 |

-continued

| No. | PHB content (%) | Nitrogen (%) | Potassium or sodium (ppm) | $M_n$ | $M_w$ |
|---|---|---|---|---|---|
| 2c | 99 | 0.22 | <30 | 382,000 | 1,090,000 |
| C2d | 90 | 1.7 | <30 | 428,000 | 1,150,000 |

The invention claimed is:

1. A method for isolating polyhydroxyalkanoates from production cells, the method comprising:
   i) disintegrating the production cells; subsequently
   ii) separating off the cell fragments from the polyhydroxyalkanoate grains using a continuous jet separator;
   iii) washing the concentrated polyhydroxyalkanoate grains with an aqueous alkali solution; and then
   iv) washing the concentrated polyhydroxyalkanoate grains with an aqueous acid.

2. The method according to claim 1, wherein the production cells are disintegrated in step i) using a high-pressure homogenizing device.

3. The method according to claim 2, wherein the homogenizing device comprises an orifice plate having at least one inlet nozzle and an orifice plate having at least one outlet nozzle, wherein mechanical energy is introduced in the intermediate space between the orifice plates.

4. The method according to claim 2, wherein the homogenizing device comprises an orifice plate having at least one inlet nozzle and an impact plate, wherein mechanical energy is introduced in the intermediate space between the orifice plate and the impact plate.

5. The method according to claim 1, wherein the production cell is a recombinant organism.

6. The method according to claim 1, wherein the polyhydroxyalkanoate is a poly(3-hydroxybutyrate) (P-3HB), a poly(4-hydroxybutyrate) (P-4HB), poly(3-hydroxy-butyrate)/co-3-hydroxyvalerate (P-3HB-co-3HV), poly(3-hydroxybutyrate)/co-4-hydroxybutyrate (P-3 HB-co-4HB), poly(3-hydroxybutyrate)/co-3-hydroxyhexanoate (P-3HB-co-3HHx) or poly(3-hydroxybutyrate)/co-3-hydroxyoctanoate (P-3 HB-co-3HO).

7. The method according to claim 1, wherein the alkali solution in stage iii) is a 0.01 to 0.5 M alkali metal hydroxide, alkali metal carbonate or alkali metal hydrogencarbonate solution.

8. The method according to claim 1, wherein the aqueous acid in stage iv) is a 0.01 to 0.5 M mineral acid, carboxylic acid or sulfonic acid.

9. The method according to claim 1, further comprising:
   v) bleaching the polyhydroxyalkanoate grains.

10. The method according to claim 9, further comprising using a 0.001 to 0.2 M hypochlorite and/or hydrogen peroxide solution in the bleaching step v).

* * * * *